(12) United States Patent
Niederhelman et al.

(10) Patent No.: US 7,357,826 B1
(45) Date of Patent: Apr. 15, 2008

(54) METHOD AND APPARATUS TO MONITOR/DETECT NODULARIZATION IN DUCTILE IRON

(75) Inventors: David A. Niederhelman, Fort Wayne, IN (US); Mark A. Bassett, Fort Wayne, IN (US)

(73) Assignee: Dana Automotive Systems Group, LLC., Toledo, OH (US)

( * ) Notice: Subject to any disclaimer, the term of this patent is extended or adjusted under 35 U.S.C. 154(b) by 534 days.

(21) Appl. No.: 10/995,544

(22) Filed: Nov. 24, 2004

Related U.S. Application Data

(60) Provisional application No. 60/524,721, filed on Nov. 25, 2003.

(51) Int. Cl.
*C21C 1/04* (2006.01)
(52) U.S. Cl. ................................ 75/386; 75/375
(58) Field of Classification Search .............. 75/375, 75/377, 386; 73/866, 597
See application file for complete search history.

(56) References Cited

U.S. PATENT DOCUMENTS

| | | | |
|---|---|---|---|
| 3,284,192 A * | 11/1966 | Spray et al. ................ | 75/377 |
| 4,164,148 A * | 8/1979 | Laforet ...................... | 73/866 |
| 4,617,830 A | 10/1986 | Pal et al. | |
| 4,913,878 A | 4/1990 | Dawson et al. | |
| 5,286,313 A | 2/1994 | Schultz et al. | |
| 5,414,510 A | 5/1995 | Schultz et al. | |
| 5,714,688 A * | 2/1998 | Buttram et al. .............. | 73/597 |
| 6,264,716 B1 | 7/2001 | Kemeny et al. | |
| 2002/0057164 A1 | 5/2002 | Davidkhanian et al. | |

* cited by examiner

*Primary Examiner*—Scott Kastler
(74) *Attorney, Agent, or Firm*—Berenato, White & Stavish

(57) ABSTRACT

The present invention is direct to a method/apparatus for verifying a nodularization process in a molten iron disposed within a ladle. The method includes the steps of: transferring the ladle with the molten iron to a nodularization area; adding an amount of magnesium to the molten iron in the ladle for producing the nodularization process in the molten iron; measuring vibration of the ladle containing the molten iron caused by the nodularization process in the molten iron; comparing the measured vibration with a predetermined level of vibration; and determining that the nodularization process occurs if the measured vibration is higher than the predetermined level of vibration.

17 Claims, 4 Drawing Sheets

METHOD AND APPARATUS TO MONITOR/DETECT NODULARIZATION IN DUCTILE IRON

This Application claims the benefit under 35 U.S.C. 119(e) of U.S. Provisional Application No. 60/524,721 filed Nov. 25, 2003 by NIEDERHELMAN et al. The disclosure of the prior application is hereby incorporated by reference herein in its entirety.

FIELD OF THE INVENTION

The present invention is directed to a method and apparatus for monitoring/detecting the nodularization step during the production of ductile iron.

BACKGROUND OF THE INVENTION

In the foundry, during the process of forming ductile iron, casting involves a reaction with molten iron and magnesium. The magnesium reaction converts some of the carbon in the iron from thin wafers to spherical nodules. (Nodularization) These nodules give ductile iron improved strength, so it is critical that this reaction occurs. Ductile iron is also known as spheroidal graphite and nodular iron. It is desirable to promote precipitation of graphite within the iron in the form of spheroids rather than interconnected flakes. Magnesium is a rare earth metal and is very desirable for the formation of acceptable nodularity. Magnesium is a very reactive metal with low vapor pressure which can result in a considerable loss of magnesium during treatment. Introduction and control of magnesium is an essential and most important step in the production of ductile iron. In practice, sufficient amounts of magnesium are often introduced to retain a certain level of residual magnesium to ensure proper nodularization. However, excessive amounts of added magnesium may cause undesirable porosity and carbides. Too little magnesium will result insufficient nodularization. Thus, detecting nodularization during controlled introduction of magnesium during the molten process is extremely beneficial.

In a high production foundry, there is an essential need for a quick control detection/monitoring tool to ensure the sufficient quality (sufficient nodularity) of the molten metal before it is poured. This will be a well understood benefit to those of ordinary skill in the art. Because ductile iron is often used in safety critical structural components of a vehicle, ensuring proper nodulation is essential. For example, ductile iron is often used to form differential cases, carriers, end yokes, flanges, slip yokes and other structural components such as steering knuckles. Failure of steering knuckles will cause an operator to lose control of the vehicle. This has serious safety implications. Thus ensuring proper nodulation during production is essential to increasing the quality of any product. The present invention poses a simple and quick solution to ensure proper nodulation during the production process before the molten metal is poured.

SUMMARY OF THE INVENTION

The present invention is direct to a method for verifying a nodularization process in a molten iron disposed within a ladle. The method includes the steps of: transferring the ladle with the molten iron to a nodularization area; adding an amount of magnesium to the molten iron in the ladle for producing the nodularization process in the molten iron; measuring vibration of the ladle containing the molten iron caused by the nodularization process in the molten iron; comparing the measured vibration with a predetermined level of vibration; and determining that the nodularization process occurs if the measured vibration is higher than the predetermined level of vibration.

DESCRIPTION OF THE INVENTION

Figure 1:
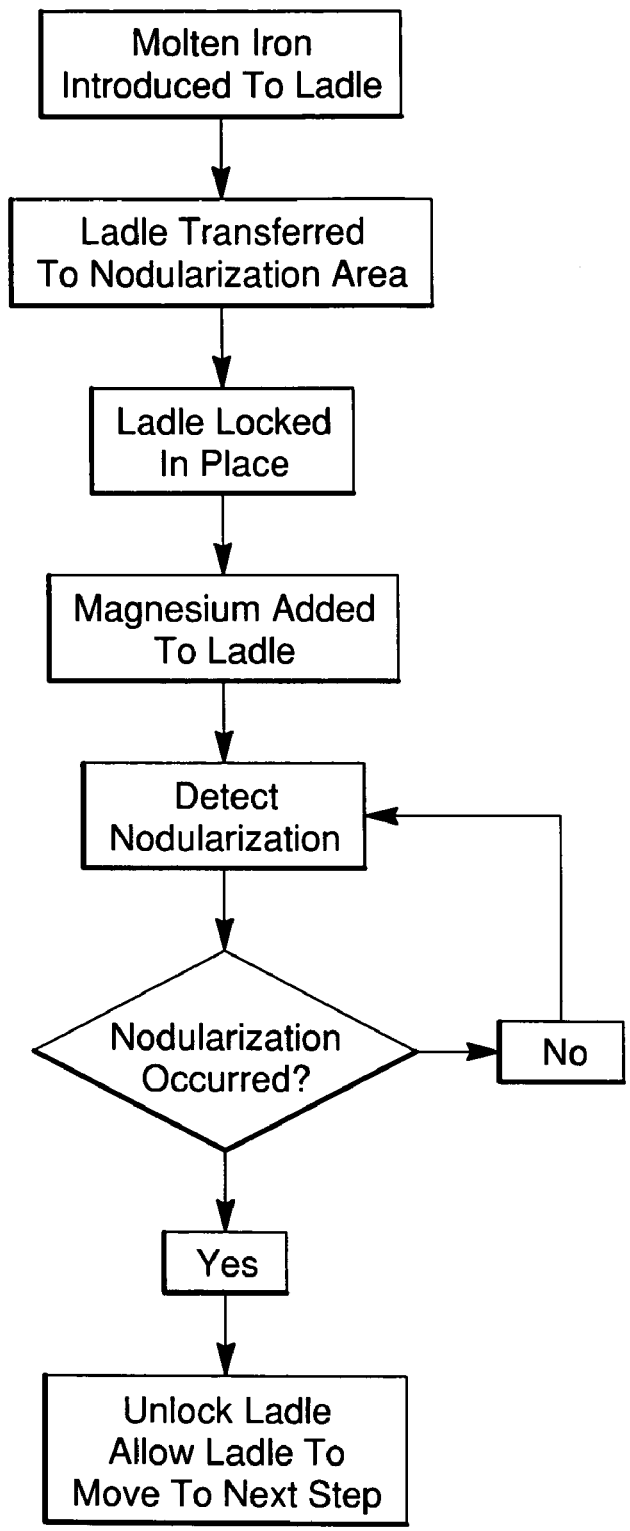
FIG. 1 is a flowchart of the control of the ladle containing molten iron and detection process according to the present invention.

FIG. 1 depicts a simply flowchart of the control of the ladle containing molten iron. Molten iron is introduced into a ladle. The ladle is transferred to a nodularization area via a rail system or other adequate transport mechanisms. Once the ladle is in the nodularization area, it is locked in place. Magnesium is then added to the molten iron in the ladle. The reaction of the addition of magnesium is monitored for detection of nodularization. If nodularization has occurred, the ladle is unlocked and allowed to be transported to the next processing step. If nodularization has not been detected, the ladle remains locked and is not allowed to move to the next processing step.

It is to be understood that it is well within the skill of one of ordinary skill in the art to construct a simple locking mechanism that reacts to a signal from a monitoring/detection system. Once such a locking and release system is in place, a simple algorithm may be employed to lock each time the ladle is introduced prior to the additional of magnesium. The algorithm is simply constructed to release the ladle in response to a signal representative of acceptable nodularization. Manual overrides may also be introduced. The details of the sensing/detecting of nodularization in the nodularization area will now be explained.

Introduction of magnesium to molten iron causes a violent reaction. As this violent reaction occurs, the ladle will vibrate. This vibration will be more severe than vibrations due to background noise and other environmental factors. The vibrations caused by the magnesium reaction can be measured and compared to vibrations occurring in the absence of the reaction in a similar environment. Detection of this vibration verifies that the molten iron in the ladle has undergone the nodularization process and the ladle permitted to be transferred down the line.

Figure 2:
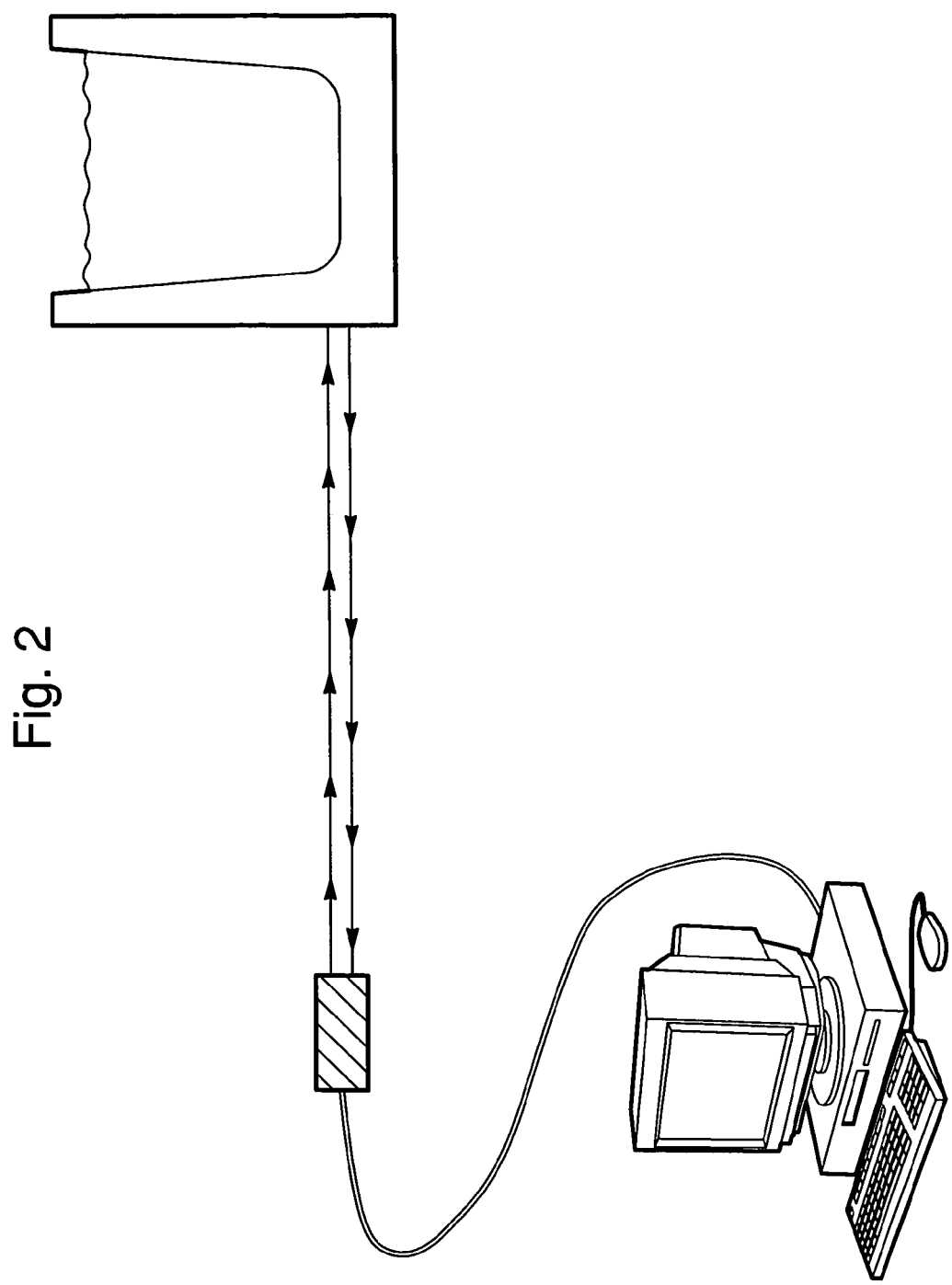
FIG. 2 is a schematic view of the apparatus to detect nodularization according to the present invention.

According to the present invention, the vibrations are sensed/detected by a laser. The laser is projected onto the ladle and reflected back to a sensing unit. (See FIG. 2). The projection/sensing unit can determine the distance of the ladle. Thus changes of this distance over time can be mapped representing the vibrations. The mapping is done by the simple calculation of (Distance)=(average velocity)*(time). A computer and software package can then compile/map/ graph the calculated distance. If the ladle is subject only to background noise, and other common environmental conditions at the nodularization staging area, a relative small or no vibration or displacement of the ladle will occur. As Magnesium is introduced into the lade reacting with the molten iron, the violent reaction will cause the ladle to vibrate and consequently be detected by the laser projector/sensor.

The laser light is preferably pulsed fort a few minutes. This will give an abundance of data points for the computer software to graph and create a mapping signature. The software will have a threshold or lower limit programmed for comparison with the sensed vibrations. The threshold may be determined by mapping/sensing the signature of the ladle with molted iron in the nodularization environment prior to the additional of magnesium. If the distances measured during vibration exceed that of the baseline signature, then successful nodularization is detected.

Figure 3:
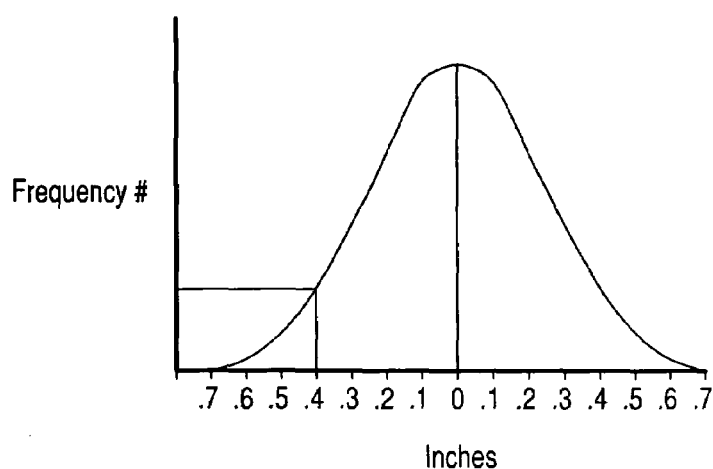
FIG. 3 is a graph depicting the displacement of the vibrations during the successful nodularization process
Figure 4A:
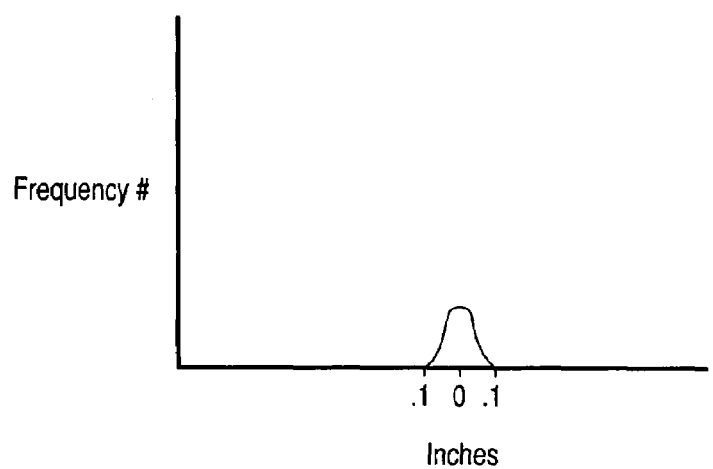
FIG. 4A is a graph representing the displacement of vibrations caused during ambient conditions at the nodularization station prior to the additional of magnesium.

Note the graph of FIG. 3 depicting the displacement of the vibrations during the successful nodularization process. In one exemplary process, the ladle will vibrate over a displacement +/−0.7 inches from a rest position as shown in FIG. 3. FIG. 4A represents the displacement of vibrations caused during ambient conditions at the nodularization station prior to the additional of magnesium. Note the much smaller displacement of +/−0.1 inches.

Figure 4B:
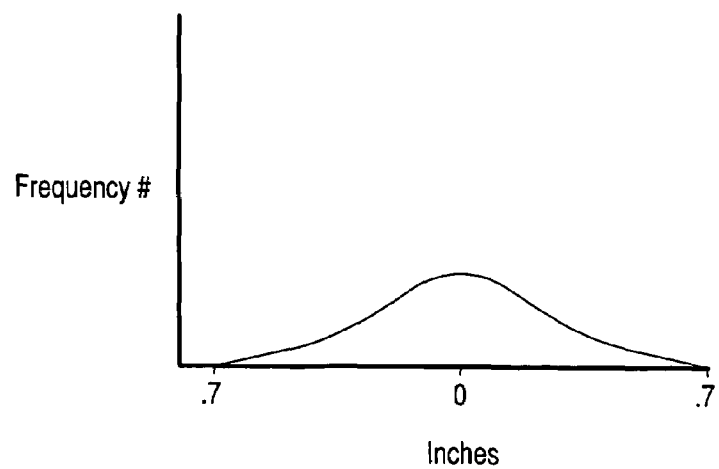
FIG. 4b is a graph representing the displacement of vibrations caused after the addition of magnesium during the magnesium reaction.

In practice, the profile or signature of vibrations of any ladle transport configuration can be mapped in ambient conditions. Such mapping will inherently account for background noise and other environmental conditions. Successful nodularization process can be mapped for a determination of a desired profile or vibration signature. By analyzing the known ambient vibration profile and a known profile indicative of successful nodularization, a threshold profile of vibration displacement can be derived to be stored in the computer software. Thus, during production, the sensed vibration can be compared to the baseline threshold to indicate successful nodularization. FIG. 4b represents the profile with the magnesium reaction.

It is noted that commercial off the shelve laser sensing technology can be employed in the present invention. So long as the laser projection and sensing unit can accurately detect distance/movement over time. Current off the shelve components are readily available for such measurement and are known to those of ordinary skill in the art. Once the laser projecting/sensing unit is installed, it simply needs to be calibrated, and the signal produced by the sensing unit sent to the computer. Software may be easily modified to recognize the signal and map the sensed distance over time. A simple algorithm may be written to simply compare the sensed vibrations to the predetermined profile for comparison. If the sensed vibrations exceed the predetermined threshold, then a successful nodularization process has occurred and the ladle will be unlocked and allowed to proceed to the next step. Otherwise the ladle is prevented from being transported to the next step.

The present invention represents a simple and quick detection mechanism to confirm that the nodularization process has occurred during the process of manufacturing ductile iron. The real time detection scheme facilitates the detection of nodularization with out interruption along the production process in the foundry and can be utilized for every batch of iron. Thus the quality of the resultant ductile iron will be greatly enhanced thus reducing the likelihood that inferior ductile iron will be produced an inadvertently incorporated into a product.

Figure 5:
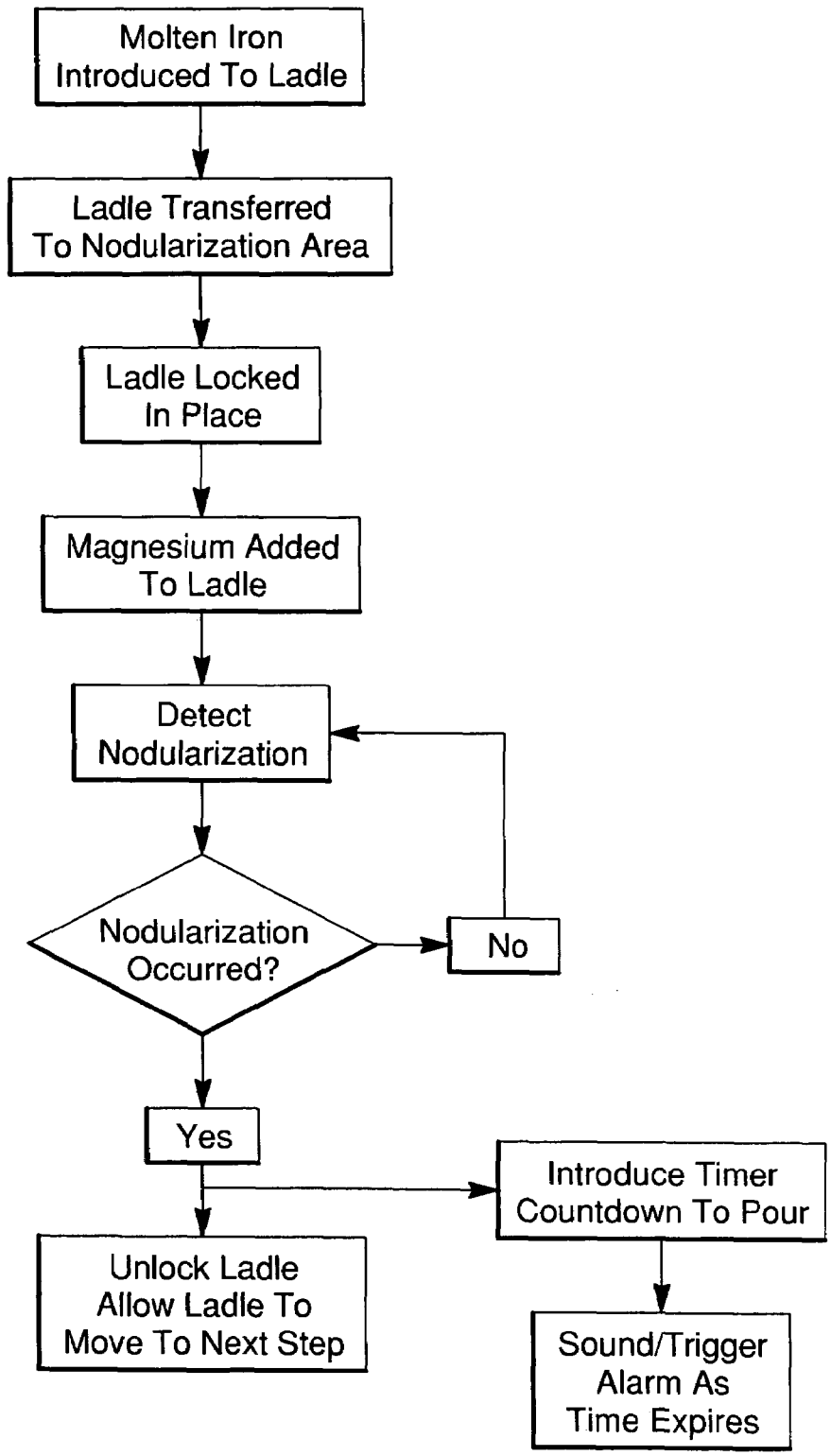
FIG. 5. a flowchart of the control of the ladle containing molten iron and detection process according to an alternate embodiment of the present invention.

The invention further contemplates utilizing a timer to establish a time in which to pour the liquid iron once nodularization is detected. Timing is very important and the ladle. FIG. 5 represents an alternative embodiment of the present invention. Once nodularization is detected, a signal is generated to start a timer to clock the time in which pour the ladle. Timers, per se, are known in the metallurgy art for other applications. Often timers are triggered in response to sensed temperatures to trigger subsequent event. Testing the magnesium content of magnesium-treated cast iron using a timer to monitor the elapsed time during cooling between a given temperature range is also known. In the present case, a time is initiated once nodularization is detected. Depending on the specific conditions in which nodularization has taken place, (volume, temperature, etc.) the desired time in which the ladle should be poured can be established. One of ordinary skill in the art is well equipped to derive the time to pour for specific foundry conditions. For routine or other foundry processes which fall into conditions of limited variance, a pre-calculated chart or look up table can be employed. The time to pour also can be calculated prior to the initiation of a given nodularization process and programmed into the control system. Detection of the nodularization/confirmation that nodularization has occurred simply starts the clock as a count down to the pre-programmed pour time. A buzzer, light or other warning system may be implemented to ensure that the ladle is poured within the specified time frame after nodularization has occurred.

While the foregoing invention has been shown and described with reference to a preferred embodiment, it will be understood by those possessing skill in the art that various changes and modifications may be made without departing from the spirit and scope of the invention.

What is claimed is:

1. A method for verifying a nodularization process in a molten iron disposed within a ladle, said method comprising the steps of:

transferring said ladle with said molten iron to a nodularization area;

adding an amount of magnesium to said molten iron in said ladle for producing said nodularization process in said molten iron;

measuring vibration of said ladle containing said molten iron caused by said nodularization process in said molten iron;

comparing said measured vibration with a predetermined level of vibration; and determining that said nodularization process occurs if said measured vibration is higher than said predetermined level of vibration.

2. The method according to claim 1, further comprising the step of:

locking said ladle to prevent transfer of said ladle during said nodularization process.

3. The method according to claim 2, wherein said step of locking said ladle responds to a signal generated during said step of determining that said nodularization process occurs.

4. The method according to claim 1, wherein said step of measuring vibration of said ladle includes measuring displacement of said ladle from a rest position.

5. The method according to claim 4, wherein said displacement is within about plus or minus seven tenths of an inch from said rest position.

6. The method of claim 4, wherein said step of measuring displacement of said ladle employs a laser sensing unit to measure said displacement of said ladle.

7. The method of claim 6, further comprising the step of calibrating said laser sensing unit prior to said step of adding said magnesium.

8. The method according to claim 7, wherein prior to adding said amount of magnesium, said step of calibrating said laser sensing unit includes pulsing said laser sensing unit and creating a mapping signature of said ladle.

9. The method according to claim 8, wherein said nodularization process is determined when a displacement of said vibration of said ladle exceeds a predetermined distance after said amount of magnesium is added.

10. The method according to claim 9, wherein said displacement of said ladle exceeds said predetermined distance when said displacement of said ladle deviates seven tenths of one inch from said mapping signature.

11. The method according to claim 1, further comprising the step of starting a timer when said nodularization process is determined.

12. The method according to claim 11, further comprising the step of pouring said molten iron after a predetermined amount of time.

13. The method according to claim 12, further comprising the step of calculating said predetermined amount of time.

14. The method according to claim 11, further comprising, the step of implementing a warning system to ensure that the ladle is poured within a specified time frame after said nodularization process has occurred.

15. The method according to claim 1, further comprising the step of utilizing a computer system to automate control of each of said steps of: transferring said ladle; adding an amount of magnesium to said molten iron; measuring vibration of said ladle; comparing said measured vibration; and determining that said nodularization process occurs.

16. The method according to claim 1, further comprising the steps of:
locking said ladle to prevent transfer of said ladle during said nodularization process in response to a signal generated during said step of determining that said nodularization process occurs;
pouring said molten iron after a predetermined amount of time after determining that said nodularization process occurs;
wherein said step of measuring vibration of said ladle includes measuring displacement of said ladle from a rest position
said step of measuring vibration of said ladle includes measuring displacement of said ladle from a rest position utilizing a laser sensing unit; and
implementing a warning system to ensure that the ladle is poured within a specified time frame after said nodularization process has occurred.

17. The method according to claim 16; further comprising the step of utilizing a computer system to automate control of each of said steps of: transferring said ladle; adding said amount of magnesium to said molten iron; measuring vibration of said ladle; comparing said measured vibration; determining that said nodularization process occurs, locking said ladle, pouring said molten iron, and implementing said warning system.

* * * * *